(12) United States Patent
Goldstein et al.

(10) Patent No.: US 6,479,019 B1
(45) Date of Patent: Nov. 12, 2002

(54) SENSOR AND SENSOR ASSEMBLY FOR DETECTING A TARGET GAS IN A BREATH SAMPLE

(75) Inventors: Mark K. Goldstein, Del Mar, CA (US); Michelle S. Oum, Chula Vista, CA (US)

(73) Assignee: Quantum Group, Inc., San Diego, CA (US)

( * ) Notice: Subject to any disclaimer, the term of this patent is extended or adjusted under 35 U.S.C. 154(b) by 0 days.

(21) Appl. No.: 09/550,557

(22) Filed: Apr. 17, 2000

Related U.S. Application Data
(60) Provisional application No. 60/129,451, filed on Apr. 15, 1999.

(51) Int. Cl.[7] .............................................. G01N 31/00
(52) U.S. Cl. ........................... 422/84; 422/83; 422/85; 422/86; 436/164
(58) Field of Search ................................ 436/133, 164, 436/136; 422/83, 84, 85, 86, 87, 88, 91; 600/309; 128/204.22; 250/243; 73/23.21; 356/437

(56) References Cited

U.S. PATENT DOCUMENTS

| | | | |
|---|---|---|---|
| 5,063,164 A | | 11/1991 | Goldstein .................... 436/169 |
| 5,573,953 A | | 11/1996 | Marnie et al. ............... 436/164 |
| 5,618,493 A | | 4/1997 | Goldstein et al. ............. 422/57 |
| 5,624,848 A | | 4/1997 | Marnie et al. ............... 436/164 |
| 5,733,505 A | | 3/1998 | Goldstein et al. ............. 422/83 |
| 5,770,793 A | * | 6/1998 | Stock ........................ 73/23.21 |
| 5,787,885 A | * | 8/1998 | Lemelson et al. ........... 600/309 |
| 5,885,843 A | * | 3/1999 | Ayers et al. ................. 436/136 |
| 5,957,127 A | * | 9/1999 | Yamamori et al. ..... 128/204.22 |
| 6,096,560 A | * | 8/2000 | Scripca et al. ............... 436/164 |
| 6,172,759 B1 | * | 1/2001 | Goldstein .................... 356/437 |
| 6,191,421 B1 | * | 2/2001 | Yamamori et al. .......... 250/243 |

* cited by examiner

*Primary Examiner*—Jill Warden
*Assistant Examiner*—Brian Sines
(74) *Attorney, Agent, or Firm*—Christie, Parker & Hale, LLP

(57) ABSTRACT

Sensor and sensor assemblies generally comprises a sensor body having a chamber disposed therein for accommodating a sensor reagent or material. The chamber is defined within the body between optically transparent body portions. The chamber is in gas flow communication with a passage used for passing a collected breath to the sensor material. A liquid or solid sensor material is disposed within the chamber and is designed to change in optical properties upon exposure to a target gas within the collected breath sample by reaction therewith. A gas permeable membrane can be disposed over the chamber opening to retain the sensor material, in the event it is liquid, and to permit the diffusion of gas from the collected breath sample to the sensor material. The sensor assembly is used with a photon source that emits photons, within a selected wavelength band, onto the chamber and sensor material, and a photon collector that is used to receive photons that exit the chamber. The photon source and photon collector can be part of the sensor assembly or can be part of a breath diagnostic assembly, of which the sensor assembly is a removable member. An optical reading means can be used to determine the change or rate of change in the optical properties, e.g., photon adsorption, of the sensor material after it is exposed to the collected breath sample. The measured change in optical properties can then be used with other gathered information, such as carbon dioxide level, to determine the level of target gas within the collected breath sample.

29 Claims, 4 Drawing Sheets

SENSOR AND SENSOR ASSEMBLY FOR DETECTING A TARGET GAS IN A BREATH SAMPLE

CROSS-REFERENCE TO RELATED APPLICATION

This patent application claims priority of U.S. Provisional Patent Application Ser. No. 60/129,451, filed Apr. 15, 1999.

FIELD OF THE INVENTION

This invention relates to an apparatus used to detect the presence of a target gas in a person's body and, more particularly, to a sensor and sensor assembly capable detecting the presence of a target gas, e.g., acetone, in a person's body by non-invasive method of breath collection and sampling.

BACKGROUND OF THE INVENTION

Chemical metabolites present within or emitted from a person's body can serves as an important indicator or biomarker of the person's physical or medical condition. Table 1 below sets forth a list of metabolites that are commonly found in a person's breath, and the respective diagnostic condition of the person providing such metabolite.

TABLE 1

| Breath Metabolite | Source | Diagnostic |
| --- | --- | --- |
| Acetaldehyde | ethanol, X-Threonine | Intoxication |
| Acetone | Acetoacetate | Diet/diabetes |
| Ammonia | Deamination of amino acids | Uremia |
| Carbon Monoxide | CH2Cl2, elevated % COHb | Indoor air pollution |
| Chloroform | Halogenated compounds | — |
| Dichlorobenzene | Halogenated compounds | — |
| Diethylamine | Choline | Intestinal bacteria |
| Hydrogen | Intestines | Lactose intolerance |
| Isoprene | Fatty Acid | Stress |
| Methanethiol | Methionine | Intestinal bacteria |
| Methylethylketone | Fatty Acid | Indoor air pollution/diet |
| O-toluidine | Carcinoma metabolite | Bronchogenic carcinoma |
| Pentane Sulfides Sulfides | Lipid peroxidation | Heart attack |
| $H_2S$ | Metabolism | Periodontal disease/ovulation |
| MES | Metabolism | Cirrhosis |
| $Me_2S$ | Infection | Trench mouth |

Accordingly, there are a number of medical conditions that can be monitored by detecting and/or measuring a person's breath metabolites. For example, the method of measuring a person's breath metabolites has widely been used by law enforcement officials for the purpose of detecting alcohol intoxication of drivers and enforcing state vehicle codes relating to driving while under the influence of alcohol. In this example, the breath metabolite of interest is a ketone, e.g., acetaldehyde.

There are many types of instruments that are currently used to detect these types of ketones such as spectroscopy, GSMS and HPLC. In addition, there are three types of low-cost detectors that can be used; namely, electrochemical, chemioptical, and semiconductor. The electrochemical cell is fairly accurate detector at levels above about 10 ppm, but is not accurate at levels below about 1 ppm. Additionally, the accuracy of readings provided by such detectors can be affected by alcohol and many other vapors, making them unsuitable for general medical use.

A tin oxide sensor known as the "Taguchi" sensor is a low-cost semiconductor sensor that is disclosed, e.g., in U.S. Pat. No. 3,676,820. However, the Taguchi sensor is known to exhibit a large sensitivity to humidity, and lacks sensitivity below 10 ppm. Therefore, making this sensor impractical for use as a breath metabolite sensor.

Thus, although breath metabolites are useful for providing a diagnostic condition of a person, the above-identified instruments and detectors known in the art are either not well suited, or do not provide a low-cost method, for providing the accurate detection or measurement of the same.

It is, therefore, desirable that a sensor and/or sensor assembly be constructed that is capable of accurately detecting and/or measuring via non-invasive method the presence of metabolites in a person's breath in low concentrations, and under humid operating conditions. It is further desired that sensors and/or sensor assemblies of this invention provide a relatively low-cost means of rapidly diagnosing the condition of a person, e.g., infants, ill and even unconscious patients.

SUMMARY OF THE INVENTION

Sensor and sensor assemblies, constructed according to principles of this invention, provide an economical and light-weight apparatus for determining the presence of, and measuring the level of, a target gas in a collected breath sample, thereby providing a practical means for diagnosing the condition of a person. The sensor assembly generally comprises a sensor body having a chamber disposed therein for accommodating a sensor reagent or material. The chamber is defined within the body between optically transparent body portions. The chamber is in gas flow communication with a passage used for passing a collected breath to the sensor material.

In one invention embodiment, the chamber is disposed radially within a wall section of a substantially tubular body, and is interposed between optically transparent body ends. This invention embodiment is useful for accommodating a liquid sensor material. In another invention embodiment, the chamber is disposed axially through the body and the sensor material is in the form of a solid film layer disposed along an inside diameter wall surface of the chamber. The ends of the body are open and, thereby, optically transparent.

The sensor material can be in the form of a liquid or solid under operating conditions, depending on particular sensor application. In either case, the sensor material is designed to produce a change in optical properties upon exposure to a target gas within the collected breath sample by reaction therewith.

In an example embodiment, the sensor material comprises one or more ingredient selected from the groups consisting of: Group 1: sodium hydroxide, potassium hydroxide, sodium carbonate, and mixtures thereof; Group 2: alcohols, dimethyl sulfoxide, tetrahydrofuran, dimethyl formamide, chloroform, and mixtures thereof; and Group 3: salicylaldehyde and its derivatives, vanilla and its derivatives, benzaldehyde and its derivatives, and mixtures thereof. Optionally, the sensor material can also include one or more ingredient selected from Group 4 consisting of molecules of the cyclodextrin family, crown ethers, and mixtures thereof. The exact chemical ingredients used will depend on the particular application and type of target gas being detected.

In the case that the sensor material is a liquid, a gas permeable membrane can be disposed over the chamber opening to both retain the liquid sensor material therein, and to permit the diffusion of gas from the collected breath sample to the sensor material.

The sensor assembly is used with a photon source that emits photons, within a selected wavelength band, onto the chamber and sensor material, and a photon collector that is used to receive photons that exit the chamber. The photon source and photon collector can be part of the sensor assembly or can be part of a breath diagnostic assembly, of which the sensor assembly is a removable member.

An optical reading means can be used to determine the change or rate of change in the optical properties, e.g., photon adsorption, of the sensor material after it is exposed to the collected breath sample. The measured change in optical properties can then be used with other gathered information, such as carbon dioxide level, to determine the level of target gas within the collected breath sample.

Sensors and sensor assemblies of this invention can, e.g., be used to non-invasively detect of the presence and level of acetone in a collected human breath sample, which can replace current invasive procedures that can be traumatic to patients, and providing more rapid, accurate and widespread information to the medical and health professionals as well as for patients.

BRIEF DESCRIPTION OF THE DRAWINGS

These and other features, aspects, and advantages of the present invention will be more fully understood when considered with respect to the following detailed description, appended claims, and accompanying figures:

DETAILED DESCRIPTION OF THE INVENTION

Sensor and sensor assemblies of this invention may comprise any of a variety of optical responding reagents that change their optical properties when exposed to a target breath constituent, airborne contaminate, or other gases containing the target gas. In example embodiments, the target gas is acetone. As used herein, a "chemioptical" sensor is one that changes light transmissivity, reflectance, or absorption in at least some wavelength range as a function of reacting with a target gas molecule such as acetone or other chemical.

Typically, these sensors darken or change color by reaction between a chemical substance in the sensor such as carbon monoxide, hydrogen, acetone, ammonia, or others. To be useful, the light absorption by the sensor should be insensitive to other components likely to be found in a person's breath, such as alcohol, acetic acid, hydrogen, and should also be relatively insensitive to changes in humidity.

Each specific sensor should selectively react with only one of the many biomarkers found in the breath. This invention preferably employs a photon monitoring of a chemical that reacts with the target gas, i.e., acetone, to undergo a change color.

The visible and/or near infrared chemioptical system of this invention is suitable for monitoring acetone and other breath constituents. Using certain cyclic aldehydes, such as salicylaldehyde and vanillin in a strong base for this purpose, sensitivity down to a 1 ppm level has been demonstrated. The color change reaction is given equation 1 below:

Equation 1

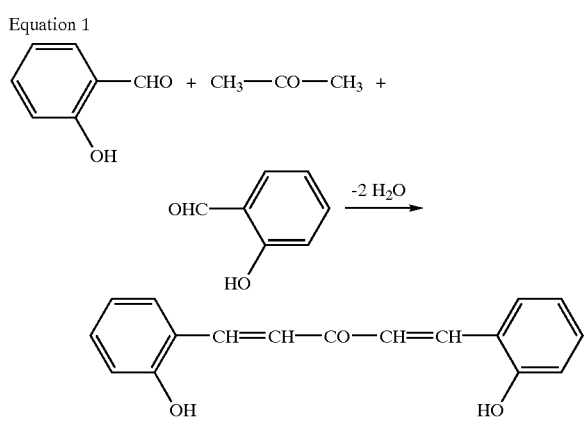

Equation 1 illustrates a condensation reaction of acetone by salicylaldehyde. Sensor and/or sensor assemblies of this invention comprising salicylaldehyde comprise a liquid salicylaldehyde solution in a plastic housing. The liquid solution is held in place by a hydrophobic membrane, such as Gortex or Millipore UPE. The liquid acetone sensor of this invention is described below in more detail.

Sensors and/or sensor assemblies of this invention employ a photon monitoring system that operates at visible or near infrared photon wavelengths. The reaction between the gaseous acetone and the liquid sensing solution can be monitored with common photon sources, such as a LED or laser diode and a photon detector such as a photo diode.

Figure 1:
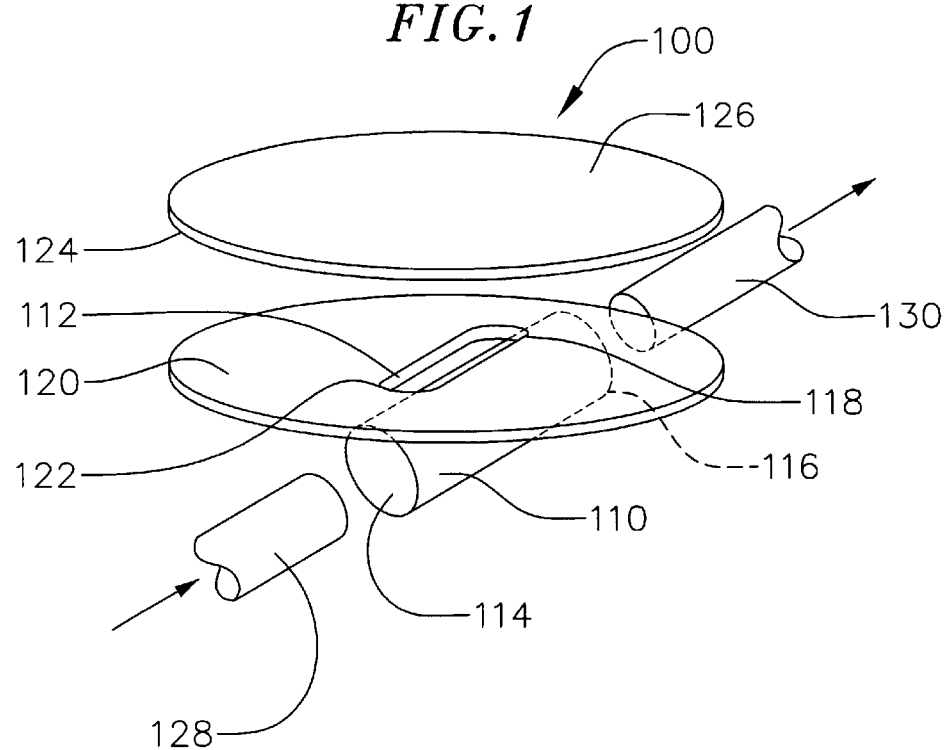
FIG. 1 is a perspective view of a sensor assembly of this invention for detecting a target gas.

FIG. 1 illustrates a sensor assembly 100, constructed according to principles of this invention, that is specially designed to react with a target gas, depending on the chemical reagent disposed within the assembly. In a preferred embodiment, the chemical reagent is selected to react with acetone vapor. The assembly 100 comprises a body 110 including a sensor reagent chamber 112 disposed therein. In an example embodiment, the body is in the shape of a cylinder. The chamber 112 extends radially into body 110 a desired depth and is defined axially by body ends 114 and 116. In an example embodiment, the body, or at least the body ends, is formed from an optically transmissive material such as plastic and the like. A volume of a desired sensor liquid reagent 118 is disposed within the chamber.

A disc-shaped base plate is connected to a side wall portion of the body 114 and includes a reagent opening 122 that is positioned over the body chamber 112. The base plate 120 can be integral with or separate from the body, and is sized and shaped to provide a support structure for a gas permeable/hydrophobic membrane 124 that is positioned over the base plate 120. The base plate can be formed from the same type of structurally rigid material used to form the body. However, the material used to form the base plate does not have to be optically transmissive.

The membrane 124 is used to isolate the liquid sensor reagent 118 from the outside environment, and is used to contain the liquid sensor reagent 118 within the body 110. The membrane 124 can be optionally supported on an opposite surface by a grid 126. The grid has a perforated configuration, or is in the form of a grill, that facilitates passage of environmental air to the membrane. The grid 126 and membrane 125 is sealed to the base plate 120 by conventional means, e.g., by thermal, ultrasonic, or other welding means.

Target gas in the air environment adjacent the membrane 126 diffuses therethrough, and into the liquid reagent 118, thereby causing a change in the reagent optical properties. Alternatively, air or gas containing the target gas molecule can be pumped through the membrane and into the chamber. A photon source 128 is positioned adjacent the body axial end 114 and is used to pass photons into the body, and into the reagent chamber 112. A suitable optical waveguide can be used, if necessary, to route photons from the photon source 128 to the body 110. Photons passed to the reagent chamber are absorbed by the liquid sensor reagent to an extent that is modified by the reaction of the target gas, e.g., acetone, thereby changing the intensity of the exiting photon beam.

A photon detecting source 130, e.g., a photo detector is positioned at the opposite body end 116 to receive photons that are passed through the chamber 112 and the liquid sensor reagent 118. A suitable optical waveguide can be used, if necessary, to route photons from the body 110 to the photon detecting source 130. The photo detecting source 130 measures the amount of change in the photon beam emerging from body end 116.

Additionally, sensor assemblies of this invention can comprise one or more waveguide or the like that is configured and connected in such manner as to provide multiple passes of photons, emitted by the photon source, through the sensor reagent, thereby enhancing photon absorption by the sensor reagent. The ability to provide photon multiple passes serves to improve the reaction time of the sensor reagent exposed to a target gas.

To increase the accuracy and flow control of sensor assemblies of this invention, the body may comprise a second chamber opening (not shown) opposite the chamber 112, along with a second membrane and grid disposed thereover. This type of dual-membrane sensor assembly responds faster to the present of a target gas due to the fact that the air or gas containing the target gas molecule can be forced through the liquid reagent 118 at a higher rate of speed than that of a single chamber opening sensor assembly, thereby increasing the rate of reaction.

The gas flow system of an acetone-containing gas through the liquid sensor reagent can be very accurate by making the gas flow rate very accurate. However, the speed passing gas through the liquid sensor reagent is limited by bubble formation, which can cause the sensor reagent to foam and provide a false reading. To control the problem of foaming, a defoaming agent can be added to the sensor reagent. Care must be taken in selecting a defoaming agent that does not interfere with the gas-sensor reagent reaction in any way. An alternative way of avoiding the potential for sensor reagent foaming is to use a solid state sensor.

Liquid sensor reagents of this invention can comprise one or more chemicals taken from one or more of the following chemical groups:

Group 1—comprising a base selected from a group including but not limited to sodium hydroxide, potassium hydroxide, sodium carbonate, and mixtures thereof;

Group 2—comprising an organic solvent and/or co-solvent selected from the group including but not limited to methanol, ethanol, propanol, dimethyl sulfoxide (DMSO), tetrahydrofuran (THF), dimethyl formamide (DMF), chloroform, and mixtures thereof;

Group 3—comprising soluble aldehydes selected from the group including but not limited to salicylaldehyde (SA) and its derivatives, vanilla (V) and its derivatives, benzaldehyde and its derivatives (all of which are specified in reaction schemes 1 to 5 below), and mixtures thereof; and Group 4—comprising supermolecular compelling molecules selected from the cyclodextrin family including alpha, beta, and gamma as well as their soluble derivatives such as hydroxymethyl, hydroxyethyl, and hydoxypropyl beta cyclodextrin, crown ethers and their derivative, and mixtures thereof.

The particular chemical formulation of a specific sensor reagent depends on the particular type of sensor application, e.g., the type of target gas molecule that is being detected. For example, sensor reagents useful for detecting the presence of acetone in a breath sample can be formed by taking one or more chemical from one each of the Group 1,2 and 3. Alternatively, sensor reagents useful for detecting the presence of acetone can be formed by including one or more chemical from Group 4 with the other chemicals of Groups 1, 2, and 3, for applications calling for a strong or enhanced sensor visual color indication.

Sensor reagents of this invention used, for example, for detecting the presence of acetone in a breath sample, can comprise: (1) in the range of from 1 to 25 percent by weight one or more Group 1 chemical; (2) in the range of from 5 to 70 percent by weight one or more Group 2 chemical; (3) in the range of from 0.3 to 8 percent by weight one or more Group 3 chemical; and (4) up to about 1 percent by weight of one or more Group 4 chemical.

The following is an example liquid phase sensor reagent formulation, prepared in accordance with the practice of this invention, useful for detecting the presence of acetone at a level as low as 4 ppm at room temperature.

EXAMPLE

An acetone liquid sensor reagent solution is prepared by combining: (1) approximately 13.33 percent by weight sodium hydroxide (Group 1); with (2) approximately 61.67 percent by weight ethanol (Group 2); (3) approximately 2.22 percent by weight SA and approximately 1.67 percent by weight V (Group 3); (4) approximately 0.5 percent by weight isoeleat CD (Group 4); and (5) the balance water. The rate of reaction between the sensor reagent and the target gas molecules is related to the concentration of sodium hydroxide, acetone, salicylaldehyde or its derivatives, and vanilla or its derivatives. The reaction rate is also related to temperature.

The liquid sensor reagent can be heated prior to exposure to the target gas, e.g., acetone, to increase the sensor response rate to acetone. Table 2, shown below, presents laboratory acetone exposure tests at 80° C. for four different liquid sensor reagent solutions. In each case, the sensor reagent solution was preheated to 80° C. a few minutes before a 10 ppm acetone gas was introduced into the sensor chamber. The acetone gas was allowed to simply diffuse into the sensing reagent without any means of a pump. An intense sensor reagent color change from yellow to orange/dark red was observed in about 5 minutes.

TABLE 2

| Solution # | Reagent | Observation on Exposed Sensing Solution | Observation on Control Sensing Solution | Relative Visual Color Change: min./max. 0 to 5 |
|---|---|---|---|---|
| 1 | SA + CD | dark orange | orange | 3 |
| 2 | SA + V + CD | red orange | yellow-orange | 5 |
| 3 | SA | orange | light yellow-orange | 1 |
| 4 | SA + V | orange | yellow | 4 |

Similar acetone sensing reagents were used to generate color response results to 0 to 30 ppm acetone at room temperature, as presented in Table 3 below. Table 3 shows results obtained from spectrophotometric scan of the (SA+V+CD) and (SA+V) reagents with acetone. The maximum absorbance (response) to acetone was shown to occur at approximately 560 nm.

TABLE 3

Time (Min.) to Change from Pantone 115U (Yellow) to Pantone (Orange) ~25% NaOH

| Acetone (ppm) | SA + V + CD (1 ml) | SA + V (1 ml) |
|---|---|---|
| 0 | no change | no change |
| 10 | 7.0 min. | 7.0 min. |
| 30 | 5.9 min. | 6.0 min. |

Table 4, below, presents "percentage changes in transmission of acetone sensing reagents at room temperature after 15 minutes" results obtained from spectrophotometric scanning of (SA+V+CD) and (SA+V) reagents with acetone. The scan was set at approximately 565 nm to simulate a common green LED that operates at 565 nm, which would be ideal for a low-cost acetone breath analyzer. Note that the relative rates of reaction depend strongly on the concentration of sodium hydroxide. At room temperature, the sensor reagent solution detected as low as 4 ppm liquid acetone in 15 minutes as indicated by the color change of the sensing solution from yellow to orange.

TABLE 4

| Acetone | ~20% NaOH | | ~10% NaOH | |
|---|---|---|---|---|
| (ppm) | SA + V + CD | SA + V | SA + V + CD | SA + V |
| 0 | 0 | 0 | 0 | 0 |
| 4 | not in test | 13.1 | not in test | not in test |
| 10 | 5 | 15.8 | 4.1 | 1.9 |
| 20 | 15.5 | 21.4 | 6.4 | 3.8 |
| 30 | 19.4 | 31.7 | 9.0 | 10.1 |

It is to be understood that sensor assemblies of this invention can be a removable part of a larger breath diagnostic assembly. In such an embodiment, the sensor body comprising the liquid sensor reagent, the membrane and grid are removable and are disposed within an assembly comprising a photon source, a photon detector.

Figure 2:
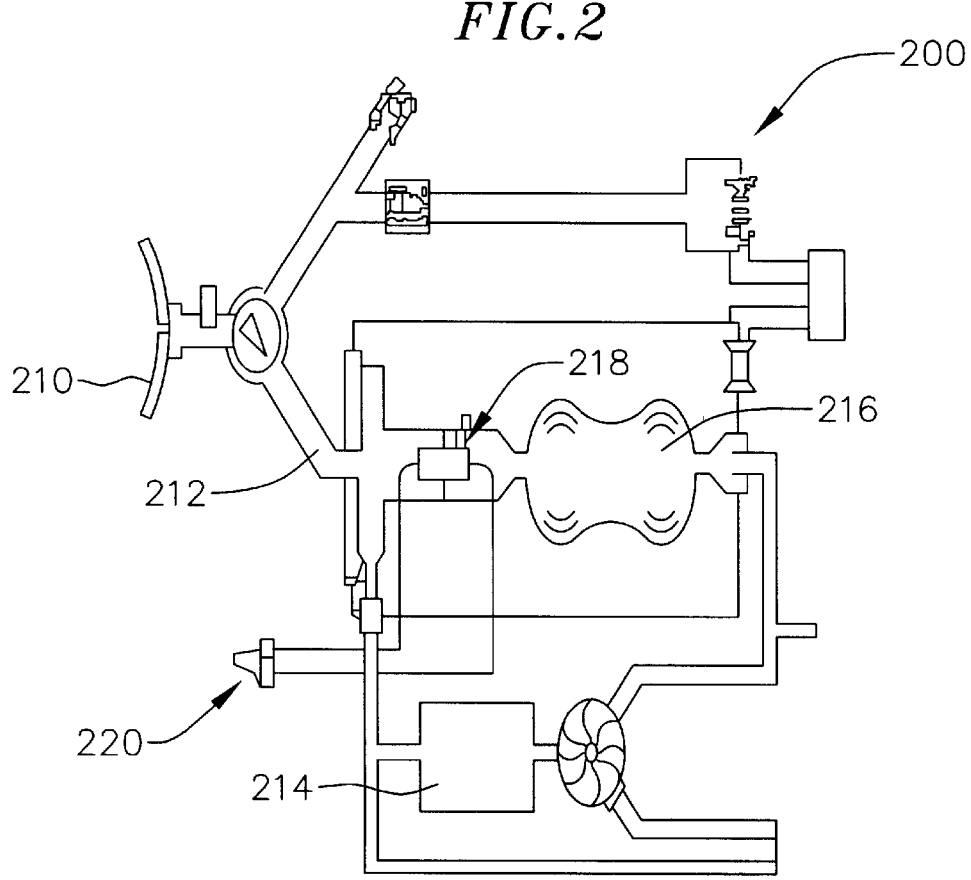
FIG. 2 is a schematic side view of a breath diagnostic assembly for measuring a target gas content in a person's breath.

FIG. 2 illustrates a breath diagnostic assembly 200, constructed according to principles of this invention, for detecting the presence of a target gas, e.g., acetone, in a human breath. The diagnostic assembly 100 comprises a mouthpiece or equivalent for collecting a volume of human breath. The mouthpiece is preferably disposable and is in gas flow communication via tubing or piping 212 with a pump 214 that is operated to circulate exhausted breath collected by the mouthpiece 210 to an expandable bladder 216.

A sensor assembly 218, comprising a liquid sensor reagent disposed within an optically transparent body, is positioned within a gas flow path between the mouthpiece 210 and the bladder 216. The sensor assembly can be removable from the breath diagnostic assembly if desired. The pump 214 circulates the exhausted breath to the acetone and carbon dioxide sensor, which change color proportional to the target gas, respectively.

A photon measuring system is connected to the sensor assembly, and comprises a photon generating source and a photon detector as discussed above. The photon measuring system reads the change of intensity of the photon absorbed by the acetone sensor reagent, calculates the target gas level (ppm), and displays the data. The assembly 200 also measures the amount of carbon dioxide in the collected sample, as this is necessary to accurately determine the amount of expired breath that has been collected. The assembly 200 is most effective when used after multiple breath samples have been taken, to build up the concentrations of acetone and carbon dioxide within the bladder 216. Then the pump 214 is actuated by a control means within the assembly 200 that can be programmed by the user.

Figure 3:
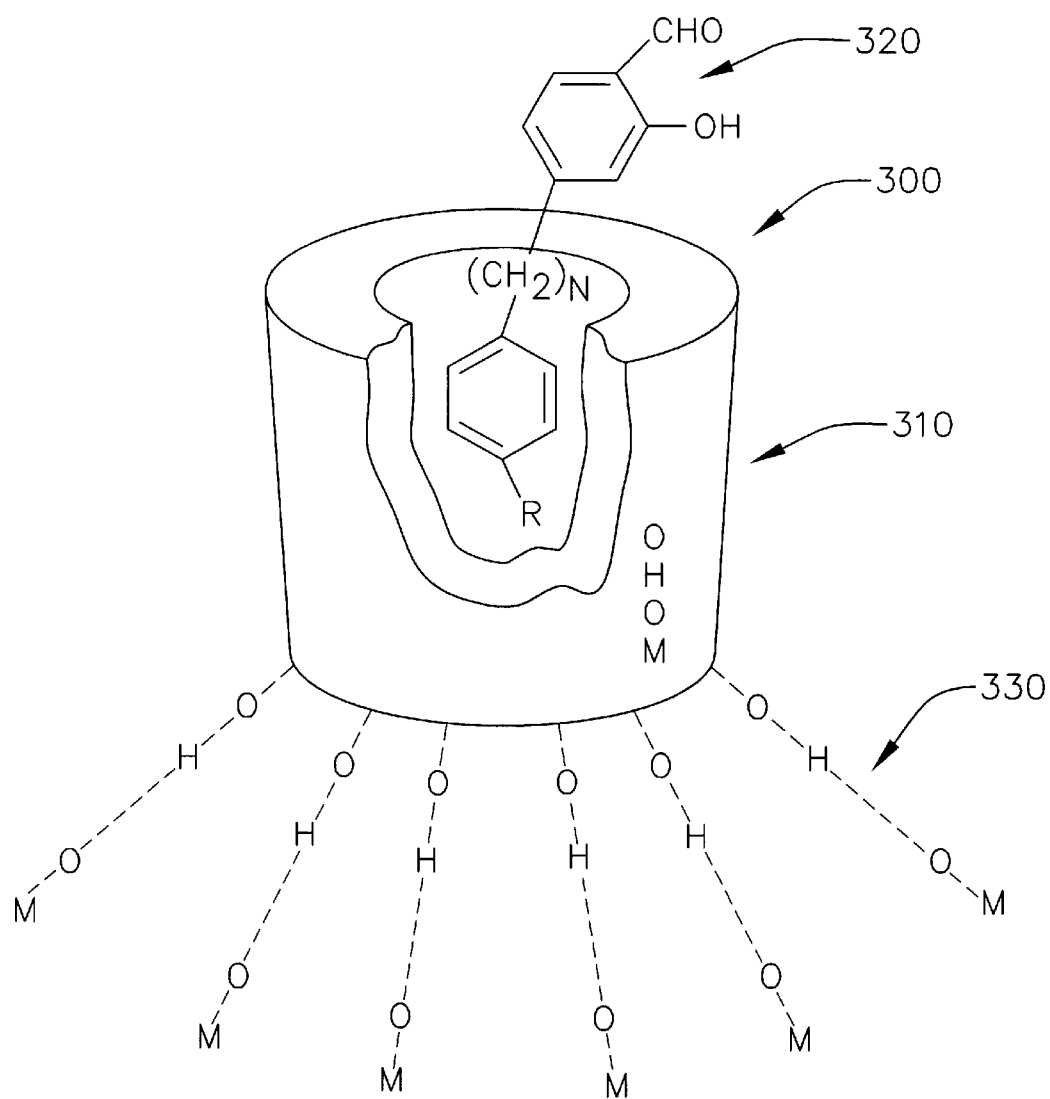
FIG. 3 is a perspective side view of a solid state sensor of this invention.

FIG. 3 is a perspective view of a cyclodextrin (CD) based solid state sensor that can be formulated for use with breath diagnostics in detecting the presence of a target gas, e.g., acetone. In an example embodiment, a thin film of CD is formed onto the surface of an optically transparent host material, e.g., a porous transparent metal oxide. Such a solid state CD based acetone sensor offers many advantages over liquid based acetone sensors. These advantages include stability, selectivity, and low activation energy. U.S. Pat. Nos. 5,063,164 and 5,618,493, which are incorporated herein by reference, describe similar CD surface modification on metal oxide surfaces such as porous silica substrates for carbon monoxide sensors, which clearly demonstrates the selectivity, the stability (long sensor life), and effective reaction temperature down to minus (−) 40° C.

An example of chemical reactions to synthesize the chemistry is given below. The solid state sensor is preferred in this case because increase sensitivity and accuracy requirements for the detection of extremely low levels of acetone in the breath. The perspective solid state CD based acetone sensor is formed by host-guest chemistry. CD and its derivatives are widely used as hosts in molecular encapsulation. The binding interaction between the host and guest depends heavily on the chemical property of the guests. The cavity of CD or its derivative is highly hydrophobic. Dumbbell-like hosts whose tail groups are more hydrophobic (simple alkyl aromatics) than the head groups are expected to have their tail groups better encapsulated inside the hydrophobic cavity of CDs; hence, positioning the head groups to reactive more selectively and rapidly with acetone at lower temperature, such as room temperature.

Several steps for synthesizing the perspective solid state CD based acetone sensor are as follow. A first step is the synthesis of the dumbbell-like reagents. A second step is preparation of the sensing solution. A third step is the impregnation of the sensing solution onto porous substrate surface or synthesis of composite thin film. Synthesis of various dumbbell-like reagents is shown in reaction schemes 1 through 5. These reactions are simple and well documented.

Reaction scheme 1 simply shows condensation reactions between salicylaldehyde/vanillin and acetone to form bischalcone 3,4. Modifications of $R^1$, $R^2$, and $R^3$ groups will lead to different starting derivatives such as 3,4- dihydroxybenzaldehyde 5, and 2,4-dihydroxybenzaldehyde, 6, which can be alkylated at the para hydroxy group so that the ortho-hydroxybenzaldeyde arrangement will be retained.

Scheme 1

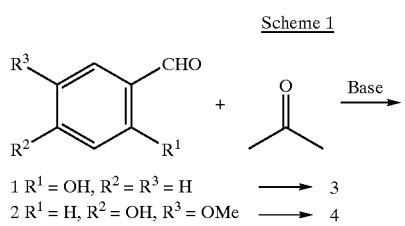

1 $R^1$ = OH, $R^2$ = $R^3$ = H ⟶ 3
2 $R^1$ = H, $R^2$ = OH, $R^3$ = OMe ⟶ 4

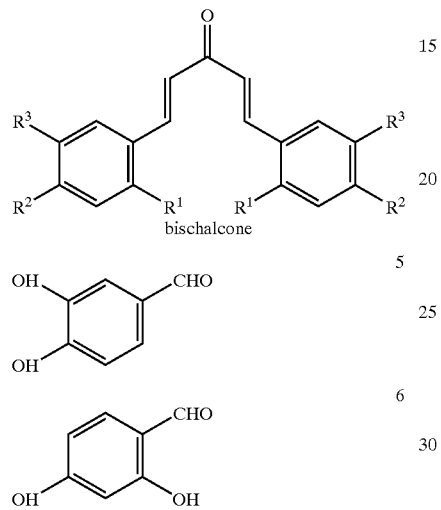

bischalcone

5

6

Reaction schemes 2 & 3 involve a series of phenyl-alkylation, 7–12, and phenoxyl-alkylation, 13–18. It is expected that the additional phenyl groups act as a site for anchoring the reagent in the CD-modified surface while the alkyl chain regulates the mobility of the head group for enhancement of the selectivity toward acetone. Tail groups in derivatives 7–18 are expected to bind better to simple aromatic in the CD.

Scheme 2

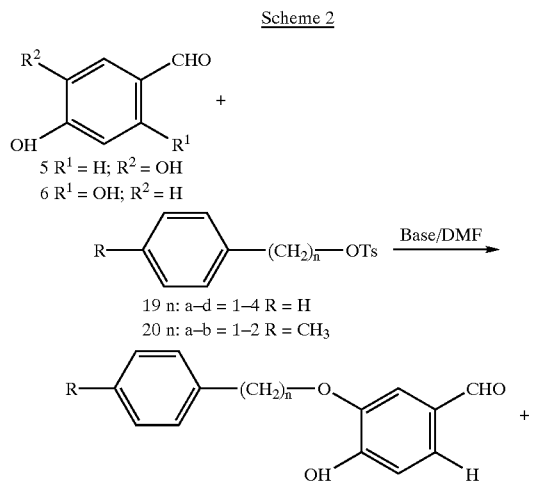

5 $R^1$ = H; $R^2$ = OH
6 $R^1$ = OH; $R^2$ = H 19 n: a–d = 1–4 R = H
20 n: a–b = 1–2 R = $CH_3$

11 $R^1$ = H: $R^2$ = OH n: a–d = 1–4 R = H
12 $R^1$ = H: $R^2$ = OH n: a–b = 1–2 R = $CH_3$

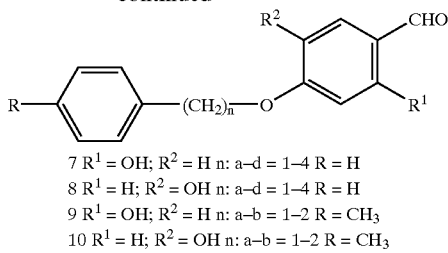

7 $R^1$ = OH; $R^2$ = H n: a–d = 1–4 R = H
8 $R^1$ = H; $R^2$ = OH n: a–d = 1–4 R = H
9 $R^1$ = OH; $R^2$ = H n: a–b = 1–2 R = $CH_3$
10 $R^1$ = H; $R^2$ = OH n: a–b = 1–2 R = $CH_3$

Scheme 3

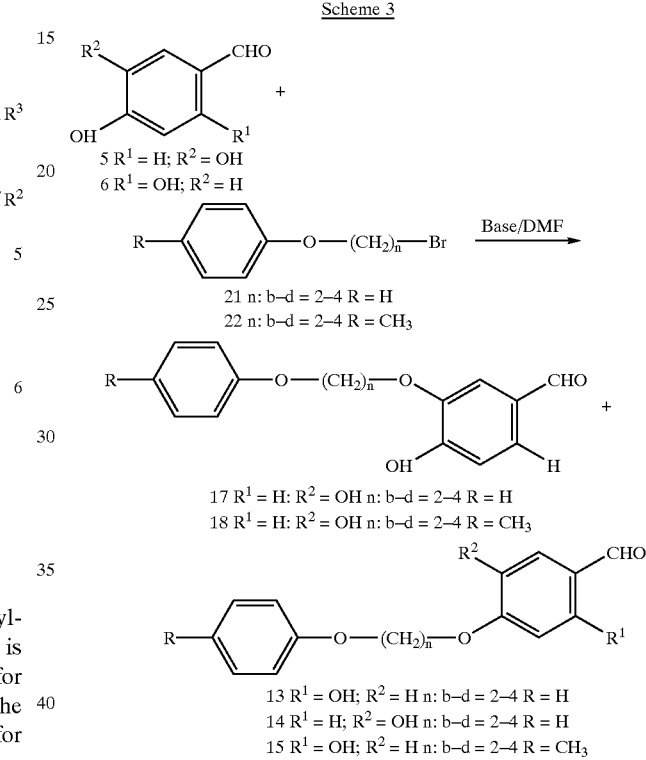

5 $R^1$ = H; $R^2$ = OH
6 $R^1$ = OH; $R^2$ = H 21 n: b–d = 2–4 R = H
22 n: b–d = 2–4 R = $CH_3$

17 $R^1$ = H: $R^2$ = OH n: b–d = 2–4 R = H
18 $R^1$ = H: $R^2$ = OH n: b–d = 2–4 R = $CH_3$

13 $R^1$ = OH; $R^2$ = H n: b–d = 2–4 R = H
14 $R^1$ = H; $R^2$ = OH n: b–d = 2–4 R = H
15 $R^1$ = OH; $R^2$ = H n: b–d = 2–4 R = $CH_3$
16 $R^1$ = H; $R^2$ = OH n: b–d = 2–4 R = $CH_3$

Reaction scheme 4 starts from commercially available precursor alcohol, which can be further tosylated to form derivatives such as 19 and 20.

Scheme 4

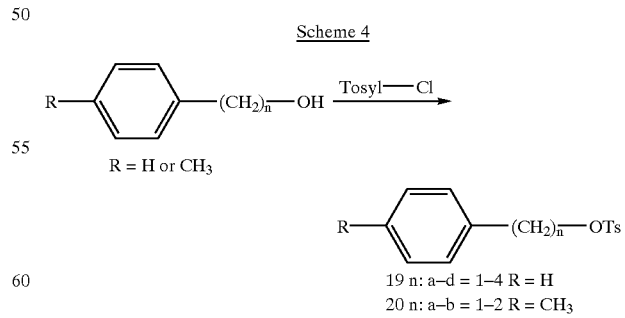

R = H or $CH_3$ 19 n: a–d = 1–4 R = H
20 n: a–b = 1–2 R = $CH_3$

Reaction scheme 5 starts from commercially available precursor alcohol, which can be further treated with base and excess of the dihalide, 23, to form 21 and 22.

Scheme 5

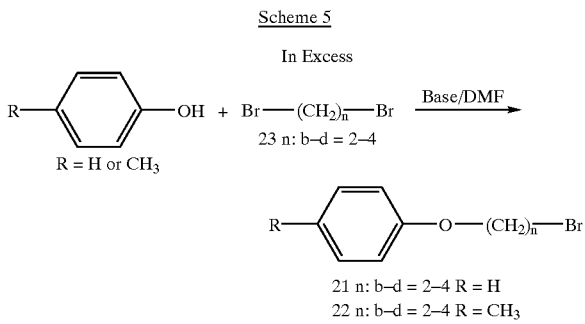

A preferred sensing reagent solution for use in sensing acetone, according to the practice of this invention, comprises approximately 13.33 percent by weight NaOH, 61.67 percent by weight ethanol, 3.89 percent by weight salicylaldehyde or its derivatives, vanillin or its derivatives, or any of the derivatives or any combination of the reagents described in the reaction schemes 1 to 5, and 0.5% of the cyclodextrins or its derivatives. The percent by weight values presented above are based on the total weight of the solution.

The procedure for impregnating the acetone sensing solution onto porous, high surface area, optically active, binary metal oxide substrates such as $ZrO_2$—$SiO_2$, $Al_2O_3$—$SiO_2$, or $TiO_2$—$SiO_2$ is similar to that use for fabricating carbon monoxide sensors. These substrates are thermally stable up to ~800° C., and are chemically stable over the pH range from 2 to 8. Porous alumina substrates are even more stable.

Figure 4A:
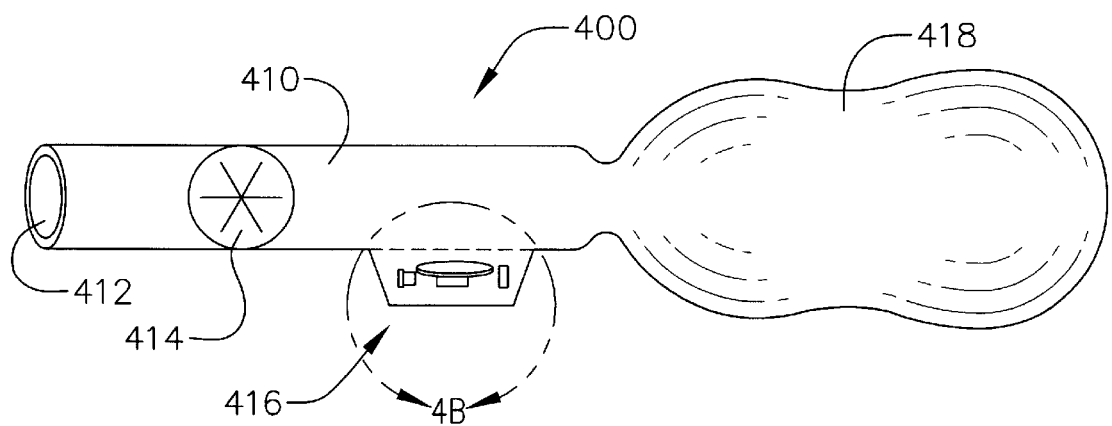
FIGS. 4A and 4B are perspective view of a breath diagnostic assembly comprising a pump and sensor assembly.
Figure 4B:
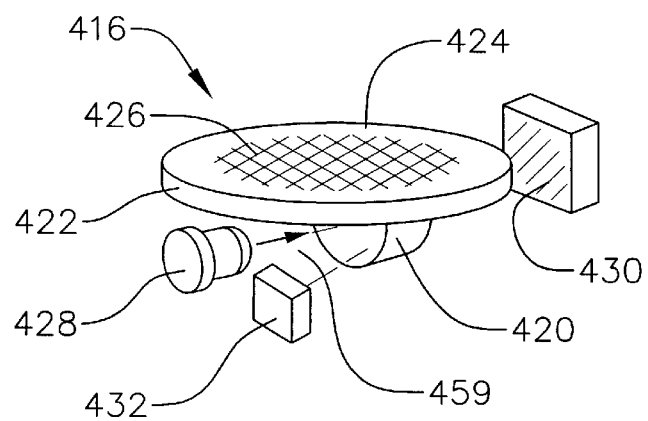

FIGS. 4A and 4B illustrate a further breath diagnostic assembly embodiment 400 of this invention comprising a body 410 having a mouthpiece 412 or equivalent at one body end for collecting a human breath sample within a gas flow chamber disposed within the body. A pump 414 is connected to the body for receiving and passing a collected breath sample through the chamber to a sensor assembly 400. The sensor assembly is positioned within the body chamber in gas flow communication with the mouthpiece. A bladder 418 or equivalent is attached to the body to collect the breath sample after it is passed by the sensor assembly.

FIG. 4B illustrates in better detail the sensor assembly 416 illustrated in FIG. 4A as comprising the substantially those components described above and illustrated in FIG. 1. The sensor assembly comprises a liquid sensor reagent solution (not shown) disposed within a sensor body 420. The body includes a sensor reagent chamber (not shown) for accommodating the liquid sensor reagent, and has body ends that are optically transparent to permit the transmission of photons therethrough. The chamber is interposed within the body between the ends so that photons passed into the body from one end passes through the sensor reagent before exiting the opposite body end.

The body includes a base plate 422 that accommodates a membrane 424 therein. A grid 426 is disposed over the membrane to maintain placement of the membrane within the baseplate and to facilitate the passage of gas thereby to the membrane. The base plate includes a reagent sensor chamber opening so that the sensor reagent disposed within the body chamber is exposed to the membrane. Thus, the breath collected in the breath diagnostic assembly body 410 is passed to the sensor assembly 416 and is allowed to diffuse through the membrane into the sensor reagent, which undergoes an optical change in response to the present of a target gas molecule, e.g., acetone.

A photon source 428, such as a laser diode, is positioned adjacent the sensor assembly body end to emit a beam of photons, preferably at a specific wavelength) into the sensor assembly. In a preferred embodiment, the emitted photon beam is close to the maximum absorption peak of the reaction product of the reaction between the target gas molecule, e.g., acetone, and the sensor reagent. A photon reflector 430 is positioned adjacent an end of the sensor assembly body opposite from the photon source to reflect photon exiting from the opposite body end back into the sensor assembly body. A photon detector 432 is positioned on the same end of the sensor assembly body as the photon source 428 and is configured to monitor the intensity of the photon beam passed back through the sensor assembly body by the reflector. The amount of the target gas within the collected breath sample is determined by monitoring the intensity of the photon beam striking the detector 432.

In an alternative embodiment, the photon detector can replace the reflector and be positioned the end of the sensor assembly body opposite the photon source. This alternative embodiment is similar to that described above and illustrated in FIG. 1. The choice to use a reflector or not depends on such issues as packaging and space constraints.

Figure 5:
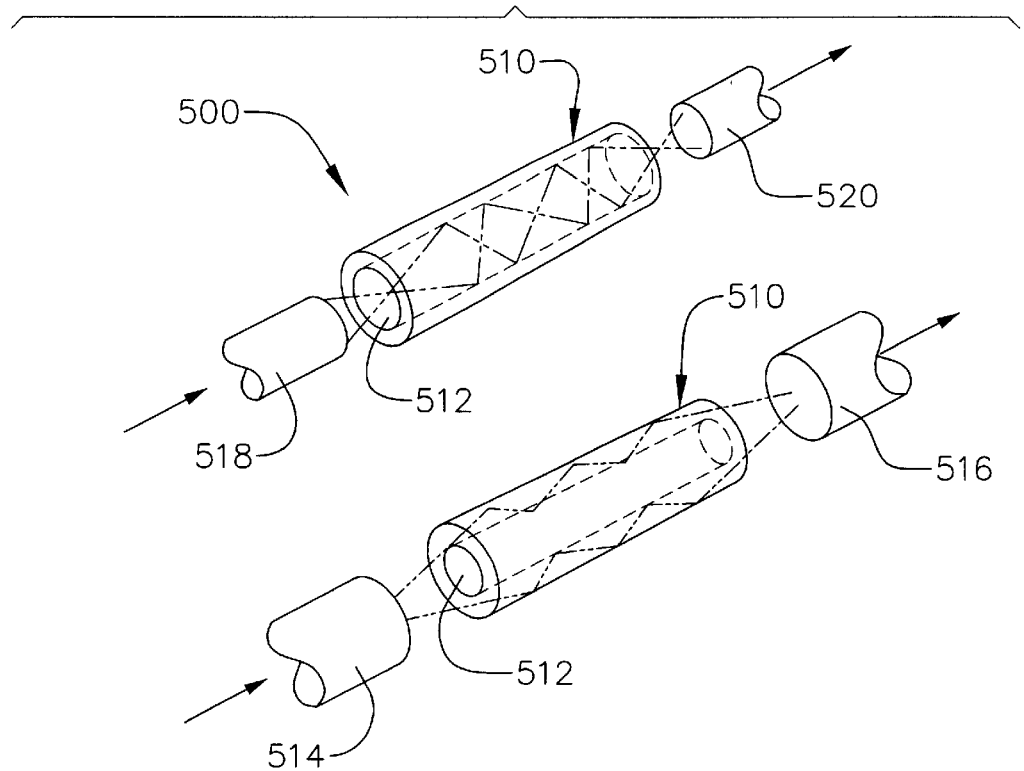
FIG. 5 is a schematic side view of a solid state tubular sensor assembly of this invention.

FIG. 5 illustrates a tubular solid state sensor assembly 500, constructed according to principles of this invention, comprising a substantially tubular body 510 having a hollow gas flow passage 512 disposed axially therethrough. The tubular body 510 is preferably made of an optically transparent material, such as clear glass, that is not permeable to gasses. The tubular body comprises a sensor reagent in the form of a thin film that is coated onto a porous inside wall surface of the gas flow passage 512. The sensor reagent can be selected from the types of materials discussed above with reference to solid state sensors.

The sensor assembly is used in conjunction with a breath collection device (not shown) so that a collected breath sample is passed through the body gas flow passage. Target gas molecules in the collected breath sample react with the solid state sensor reagent to cause a change in the sensor optical properties. A photon source 514 is positioned adjacent one axial end of the tubular body 510 and emits a photon beam through the gas flow chamber. In an example embodiment, the photon source 514 passes a photon beam many times through the gas flow chamber as the collected breath sample is passed through the gas flow passage. A photon detector 516 is positioned adjacent an axial end of the tubular body opposite from the photon source for collecting photons exiting the gas flow passage, and for measuring the change in photon intensity caused by the reaction of the sensor reagent.

Alternatively, optical waveguides 518 and 520 can be interposed between respective ends of the tubular body and the photon source 514 and photon detector 516 if necessary to accommodate any existing assembly packaging and/or spacial constraints. Also, a reflector (not shown) can be positioned at an end of the tubular body opposite the photon source (replacing the photon detector), and the photon detector can be positioned adjacent the photon source, if required for packaging or the like.

Figure 6:
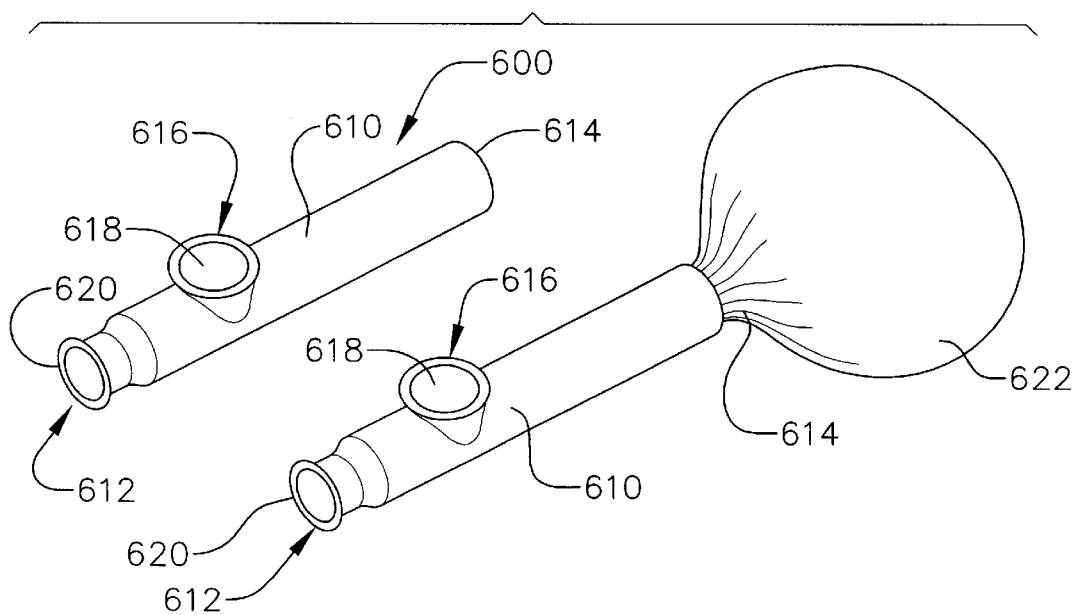
FIG. 6 is a perspective view of a sensor assembly comprising a breath collection means.

FIG. 6 illustrates a breath diagnostic assembly 600, constructed according to principles of this invention, comprising a tubular body 610 formed from a suitably rigid structural material, e.g., plastic. The body comprises a substantially hollow gas flow passage disposed therethrough extending between first and second body axial ends 612 and 614. A sensor assembly 616 is positioned within the body such that a sensor reagent contained therein is exposed to gas that is passed through the gas passage. The sensor assembly 616 is substantially similar to that described above and illustrated in FIG. 1 comprising, a liquid sensor reagent and a gas permeable membrane interposed between the liquid sensor reagent and the gas flow passage. Alternatively, the sensor assembly 616 can comprise a solid state sensor as described above, including a sensor reagent coated onto a glass or other form of optically clear material.

The tubular body 610 includes a window 618 for permitting viewing of the sensor reagent within the sensor assembly. The sensor reagent can be selected from those described above to provide an indication of the presence of a target gas within a collected breath sample by undergoing a color change.

A mouthpiece 620 or equivalent is positioned at the body end 612 for collecting a breath sample and passing the same through the gas flow chamber. As the breath sample is passed through the chamber, it comes into contact with the sensor assembly 616 and any target gas molecules contained therein reacts with the sensor reagent to cause a color change. A bladder 622 or equivalent is positioned at an opposite end 614 of the tubular body for collection of the breath sample. The presence of a target gas molecule within the collected breath sample can be determined by simply viewing the window and looking for a color change, or by using an optical reader to determined the change in optical properties of the sensor reagent behind the window.

Each of the sensor assemblies discussed above and illustrated can be used in conjunction with an optical reading means, e.g., an electoptical reader, and can be operated via a controller in the following manner. A controller is programmed to monitor change in optical properties of the sensor reagent and provide an analysis of the target gas concentration in view thereof via programmed information. The controller, via a microprocessor, can monitor the change of the sensor reagent optical properties and determined target gas concentration therefrom by using either a stored table of target gas levels as a function of optical properties, e.g., light absorption, or by calculating the same from stored equations. The controller also monitors the strength of the signal from a light detector and verifies that a light source and the light detector are properly functioning, along with the appropriate portions of the controller. If everything is in good order, the controller causes a display to appear on a numeric display that informs the operator that the device is functioning properly. Subsequently, the controller can be configured to provide via numeric display the approximate measured concentration of target gas in the collected breath sample.

Sensor and sensor assemblies of this invention permit the non-invasive measurement of acetone and carbon monoxide to determine the metabolic health condition of a person. This is accomplished by collecting and or concentrating the component gas to be monitored to determine the concentration normalized to end-expired air and thus the health condition. For example, using this invention, one can determined why a victim is unconscious by measuring the level of acetone in the exhaled breath, and provide any necessary treatment. This invention does so by using a chemoptical sensor, which changes its optical properties (such as darkens) in the presence of a target biomarker by chemical reaction. A beam of photon is passed through a high surface area of the sensor many times to increase the sensitivity.

Another embodiment of this invention uses a balloon or bladder to collect the breath for easy self-diagnostic purposes. In such embodiment, the collected breath sample is passed through a transparent tube containing the sensor. A flow-limiting orifice us used to assure that the sensor is exposed to the captured breath. A carboxyhemoglobin level is determined by measuring the sensor darkening over a short period of time. The sensor assembly is disposable and comes sealed in a package having a moisture content similar to that of exhaled breath. The technique is quick and inexpensive, greatly increasing the opportunity to employ this test for diagnostic purposes to prevent serious and sometimes fatal consequences of a misdiagnosis. The acetone sensor may be used in any gases environment to detect that vapor's concentration.

Sensor assemblies of this invention provide a relatively inexpensive and light-weight component that is capable of quickly assessing and diagnosing the condition of a person via the non-invasive method of collecting a breath sample. Practically, sensor assemblies of this invention provide for the quick detection of a variety of metabolites, specifically acetone, in a person's breath, which may be used to quickly assess the degree of alcohol intoxication or carbon Tonoxide poisoning. Sensor systems of this invention, therefore, will help to uncover cases of carbon monoxide poisoning that could otherwise either be misdiagnosed or go undetected.

Many modifications and variations of sensor assemblies as specifically discussed and illustrated will be apparent to those skilled in the art. For example, certain optical lenses and filters can be used in conjunction with the photon sources and photon detectors if necessary to obtain a desired objective. Also, sensor assemblies can be configured having different physical arrangements, depending on the particular packing application or application spacial constraints. It is therefore to be understood that within the scope of the following claims, that sensor assemblies of this invention can be practiced otherwise than as specifically described.

What is claimed is:

1. A sensor assembly for use in determining the presence of a target gas within a breath sample comprising:
    a sensor body having a chamber disposed therein, the chamber extending between body portions that are optically transparent, the chamber being in gas flow communication with a passage for passing a collected breath sample therethrough;
    a sensor material disposed within the chamber, the sensor material being reactive with a target gas in a collected breath sample to produce a change in sensor optical properties, the sensor material comprising one or more ingredients selected from each of the following groups consisting of:
        Group 1: sodium hydroxide, potassium hydroxide, sodium carbonate, and mixtures thereof;
        Group 2: alcohols, dimethyl sulfoxide, tetrahydrofuran, dimethyl formamide, chloroform, and mixtures thereof; and
        Group 3: salicylaldehyde and its derivatives, vanilla and its derivatives, benzaldehyde and its derivatives, and mixtures thereof.

2. The assembly as recited in claim 1 wherein the sensor material further comprises one or more ingredients selected from Group 4 consisting of molecules of the cyclodextrin family, crown ethers, and mixtures thereof.

3. The assembly as recited in claim 2 wherein the sensor material comprises:
    in the range of from 1 to 25 percent by weight of one or more Group 1 ingredients;
    in the range of from 5 to 70 percent by weight of one or more Group 2 ingredients;
    in the range of from 0.3 to 8 percent by weight of one or more Group 3 ingredients; and
    up to about 1 percent by weight of one or more Group 4 ingredients.

4. The assembly as recited in claim 1 wherein the sensor material is a liquid under operating conditions and the body chamber includes an opening to the passage, and wherein the sensor assembly further comprises means disposed over the chamber opening and interposed between the sensor material and the passage to both retain the liquid sensor material within the chamber and permit the diffusion of gas from the passage to the sensor material.

5. The assembly as recited in claim 1 wherein the sensor material is in solid form under operating conditions and is disposed onto a porous substrate.

6. The assembly as recited in claim 5 wherein the porous substrate is the body, wherein the body has a substantially tubular form and the chamber extends axially therethrough, and wherein the sensor material is disposed along an inside diameter wall surface of the body.

7. The assembly as recited in claim 1 further comprising:
a photon source positioned adjacent an optically transparent body portion for directing photons into the chamber and into the sensor material; and
a photon collector positioned adjacent the same or different optically transparent body portion as the photon source for receiving photons from the chamber and the sensor material.

8. The assembly as recited in claim 7 wherein the photon source and photon collector are positioned adjacent the same optically transparent body portion, and comprising a reflector positioned at an optically transparent body portion opposite from the photon source and photon collector.

9. The assembly as recited in claim 1 further comprising means for measuring the change in optical properties of the sensor material when exposed to the target gas, and for determining the level of target gas within the breath sample from the measured change in optical properties.

10. The assembly as recited in claim 1 further comprising:
means for collecting a breath sample;
means for storing the collected breath sample; and
means for controlling the release of the collected breath sample from the means for storing to the passage for contact with the sensor material.

11. A sensor assembly for measuring the concentration of a target gas in a human breath sample comprising:
a sensor body having a chamber disposed therein, the chamber extending between body portions that are optically transparent and having an opening to a surrounding environment outside of the body;
a sensor material disposed within the chamber, the sensor material being liquid under operating conditions and being reactive with a target gas to produce a change in sensor material optical properties;
a gas permeable membrane disposed over the chamber opening and interposed between the sensor material and the environment outside of the body;
means for collecting and passing a sample of a human breath to the membrane for passing to sensor material;
a photon source disposed adjacent the body for emitting photons into the chamber and into the sensor material;
a photon collector disposed adjacent the body for receiving photons exiting the chamber.

12. The assembly as recited in claim 11 wherein the sensor material comprises one or more ingredients selected from each of the following groups consisting of:
Group 1: sodium hydroxide, potassium hydroxide, sodium carbonate, and mixtures thereof;
Group 2: alcohols, dimethyl sulfoxide, tetrahydrofuran, dimethyl formamide, chloroform, and mixtures thereof; and
Group 3: salicylaldehyde and its derivatives, vanilla and its derivatives, benzaldehyde and its derivatives, and mixtures thereof.

13. The assembly as recited in claim 12 wherein the sensor material further comprises at least one supermolecular compelling molecule from Group 4 consisting of molecules of the cyclodextrin family, crown ethers, and mixtures thereof.

14. The assembly as recited in claim 13 wherein the sensor material comprises:
in the range of from 1 to 25 percent by weight of one or more Group 1 ingredients;
in the range of from 5 to 70 percent by weight of one or more Group 2 ingredients;
in the range of from 0.3 to 8 percent by weight of one or more Group 3 ingredients; and
up to about 1 percent by weight of one or more Group 4 ingredients.

15. The assembly as recited in claim 11 wherein the body is substantially tubular and the chamber extends radially into the body from at least one wall surface, and wherein the photon source and photon detector are each positioned adjacent an opposite axial end of the body that is optically transparent.

16. The assembly as recited in claim 11 wherein the body is substantially tubular and the chamber extends radially into the body from at least one wall surface, and wherein the photon source and photon detector are each positioned adjacent one axial end of the body that is optically transparent, and wherein a reflector is positioned adjacent an opposite axial end of the body that is optically transparent.

17. The assembly as recited in claim 11 further comprising a optical waveguide positioned adjacent the body for receiving photons exiting the body and passing the received photons back into the body and the sensor material.

18. The assembly as recited in claim 11 Further comprising:
means for measuring the rate of change of optical properties of the sensor material when exposed to the target gas in the collected breath sample;
means for measuring the level of carbon dioxide in the collected breath sample; and
means for determining the level of target gas with the collected breath sample.

19. The assembly as recited in claim 18 wherein the means for measuring comprises a circuit to measure and analyze the rate of change of optical properties of the sensor material, and wherein the means for determining comprises a microprocessor to calculate the amount of the target gas in the collected breath sample by measuring the level of carbon dioxide in the collected sample to determine the amount of end-expired breath capture.

20. A sensor assembly for measuring the concentration of a target gas in a human breath sample comprising:
a sensor body having a chamber disposed therein, the chamber extending between body portions that are optically transparent and having an opening to a surrounding environment outside of the body;
a liquid sensor material disposed within the chamber, the sensor material being reactive with a target gas to produce a chemoptical response, the sensor material comprising one or more ingredients selected from each of the following groups consisting of:
Group 1: sodium hydroxide, potassium hydroxide, sodium carbonate, and mixtures thereof;

Group 2: alcohols, dimethyl sulfoxide, tetrahydrofuran, dimethyl formamide, chloroform, and mixtures thereof; and Group 3: salicylaldehyde and its derivatives, vanilla and its derivatives, benzaldehyde and its derivatives, and mixtures thereof; and optionally including one or more ingredients selected from Group 4: consisting of molecules of the cyclodextrin family, crown ethers, and mixtures thereof;

a gas permeable membrane disposed over the chamber opening and interposed between the sensor material and the environment outside of the body;

means for collecting and passing a sample of a human breath to the membrane for passing to sensor material;

a photon source disposed adjacent the body for emitting photons into the chamber and into the sensor material;

a photon collector disposed adjacent the body for receiving photons exiting the chamber; and means for measuring the rate of change of sensor material optical properties when exposed to the collected breath sample.

21. The assembly as recited in claim 20 wherein the sensor material comprises:

in the range of from 1 to 25 percent by weight of one or more Group 1 ingredients;

in the range of from 5 to 70 percent by weight of one or more Group 2 ingredients;

in the range of from 0.3 to 8 percent by weight of one or more Group 3 ingredients;

up to about 1 percent by weight of one or more Group 4 ingredients.

22. A method for determining the level of target gas in a collected breath sample comprising the steps of:

collecting a sample of breath;

passing the collected breath sample to a sensor assembly comprising a sensor material disposed within a body having one or more optically transparent portions, wherein the sensor material is disposed within the body so that it is exposed to the breath sample passed to the sensor assembly;

directing photons into the body and sensor material by a photon source;

receiving photons exiting the body and sensor by a photon collector;

measuring a change in sensor material optical properties when exposed to the collected breath sample; and determining the level of target gas within the collected breath sample from the measured optical properties;

wherein during the passing step the sensor material undergoes a chemical reaction upon exposure to the target gas that produces an optical change, wherein the sensor material is a liquid at operating conditions and comprises one or more ingredients selected from each of the following groups consisting of:

Group 1: sodium hydroxide, potassium hydroxide, sodium carbonate, and mixtures thereof;

Group 2: alcohols, dimethyl sulfoxide, tetrahydrofuran, dimethyl formamide, chloroform, and mixtures thereof; and Group 3: salicylaldehyde and its derivatives, vanilla and its derivatives, benzaldehyde and its derivatives, and mixtures thereof.

23. The method, as recited in claim 22 wherein the sensor material further comprises one or more ingredients selected from Group 4 consisting of molecules of the cyclodextrin family, crown ethers, and mixtures thereof.

24. The method as recited in claim 22 further comprising, during the passing step, the sensor material is disposed within a chamber in the body, and the target gas within the collected breath sample is allowed to diffuse through a gas permeable membrane disposed over an opening to the chamber before reaching the sensor material.

25. The method as recited in claim 22 wherein the step of measuring is performed by an optical reading means, and the step of determining is performed by a microprocessor, and wherein during the step of determining the level of carbon dioxide is calculated.

26. The method as recited in claim 25 wherein the step of determining comprises comparing the measured change in sensor material optical properties to stored value for the target gas, and using the measured level of carbon dioxide to correct for the percent breath collected.

27. The method as recited in claim 26 further comprising the step of calculating the metabolism condition of a person providing the collected breath sample.

28. The method as recited in claim 22 further comprising the step of storing the collected breath sample and passing the collected sample to the sensor assembly.

29. The method as recited in claim 22 further comprising the step of receiving photons exiting from the sensor assembly and passing the received photons back into the sensor assembly.

* * * * *